United States Patent
Dewey

(10) Patent No.: US 10,149,771 B2
(45) Date of Patent: Dec. 11, 2018

(54) B-SHAPED INTERBODY IMPLANT

(71) Applicant: Warsaw Orthopedic, Inc., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 159 days.

(21) Appl. No.: 14/931,047

(22) Filed: Nov. 3, 2015

(65) Prior Publication Data
US 2017/0119544 A1    May 4, 2017

(51) Int. Cl.
A61F 2/44    (2006.01)
A61F 2/30    (2006.01)

(52) U.S. Cl.
CPC ............ *A61F 2/4425* (2013.01); *A61F 2/442* (2013.01); *A61F 2/4455* (2013.01); *A61F 2002/3055* (2013.01); *A61F 2002/30186* (2013.01); *A61F 2002/30471* (2013.01); *A61F 2002/30476* (2013.01); *A61F 2002/30518* (2013.01); *A61F 2002/30523* (2013.01); *A61F 2002/30538* (2013.01); *A61F 2002/30624* (2013.01); *A61F 2002/30629* (2013.01); *A61F 2002/30904* (2013.01); *A61F 2002/4475* (2013.01); *A61F 2220/0091* (2013.01); *A61F 2230/0032* (2013.01)

(58) Field of Classification Search
CPC ............................................ A61F 2/44–2/447
See application file for complete search history.

(56) References Cited

U.S. PATENT DOCUMENTS

| | | | | |
|---|---|---|---|---|
| 6,482,233 | B1 * | 11/2002 | Aebi | A61F 2/4465 623/17.11 |
| 6,582,431 | B1 * | 6/2003 | Ray | A61B 17/025 606/247 |
| 2008/0065219 | A1 * | 3/2008 | Dye | A61F 2/4465 623/17.16 |
| 2009/0254182 | A1 * | 10/2009 | Kovarik | A61F 2/447 623/17.11 |
| 2011/0230970 | A1 * | 9/2011 | Lynn | A61F 2/442 623/17.16 |
| 2012/0310354 | A1 * | 12/2012 | Ullrich, Jr. | A61F 2/4465 623/17.16 |
| 2013/0041471 | A1 * | 2/2013 | Siegal | A61F 2/442 623/17.16 |
| 2013/0079883 | A1 * | 3/2013 | Butler | A61F 2/4425 623/17.16 |
| 2013/0345814 | A1 * | 12/2013 | Walkenhorst | A61B 17/7059 623/17.16 |
| 2016/0361177 | A1 * | 12/2016 | Biedermann | A61F 2/446 |

* cited by examiner

*Primary Examiner* — Nicholas Plionis

(57) ABSTRACT

A B-shaped implant for insertion into a disc space between adjacent vertebral bodies. The implant includes first and second projecting lobes configured to sit on bony prominences adjacent a posterior rim of a lower one of the vertebral bodies. A concave recess between the two projecting lobes is configured to avoid impact with the vertebral foramen. An anterior portion wall connects ends of the B-shaped implant, cooperating with the projecting lobes to define fill spaces. The fill spaces can be packed with bone growth material. The implant can be expandable, made of rotatable interconnected links, which can be inserted into the disc space in an unexpanded position, and expanded in the disc space to an expanded position.

17 Claims, 9 Drawing Sheets

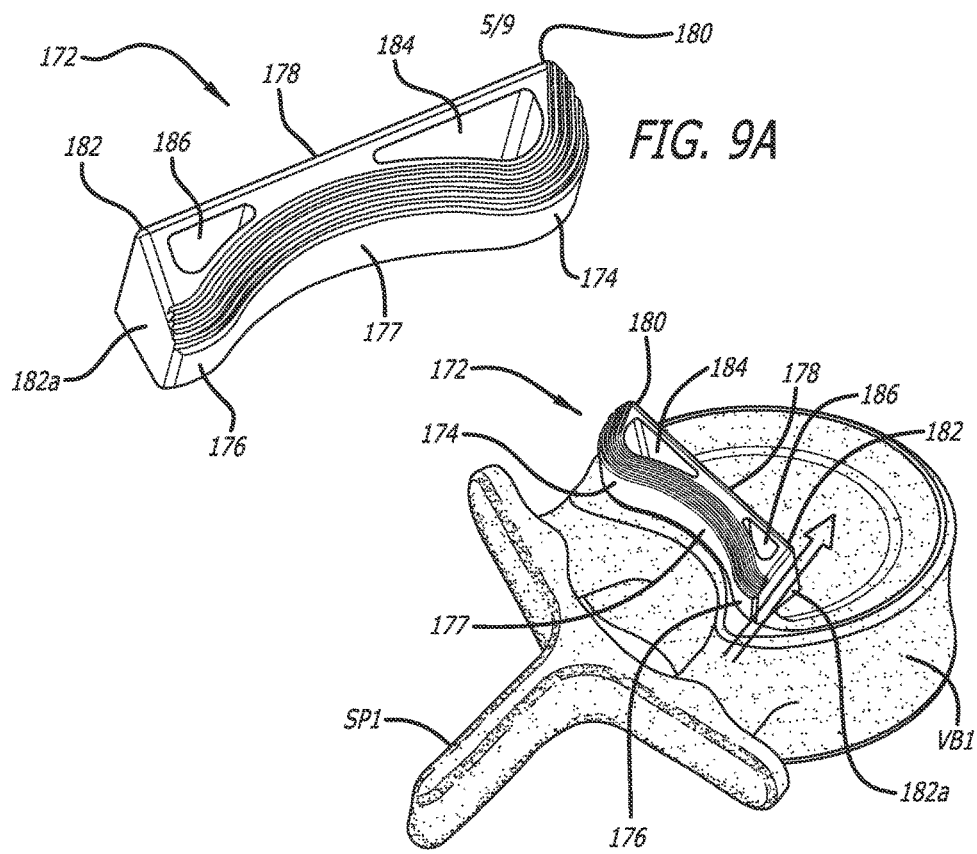
FIG. 9A
FIG. 9B
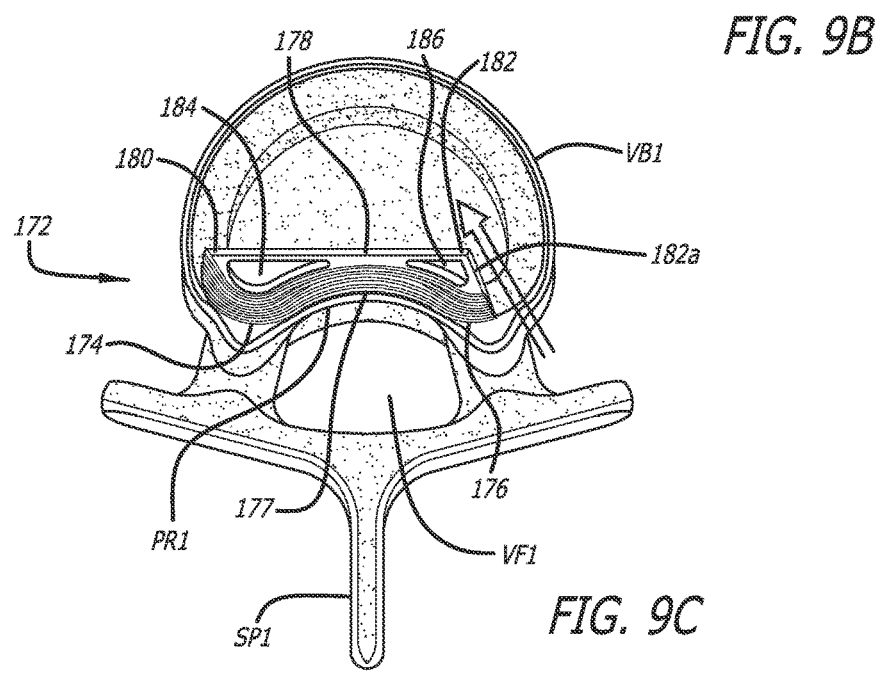
FIG. 9C

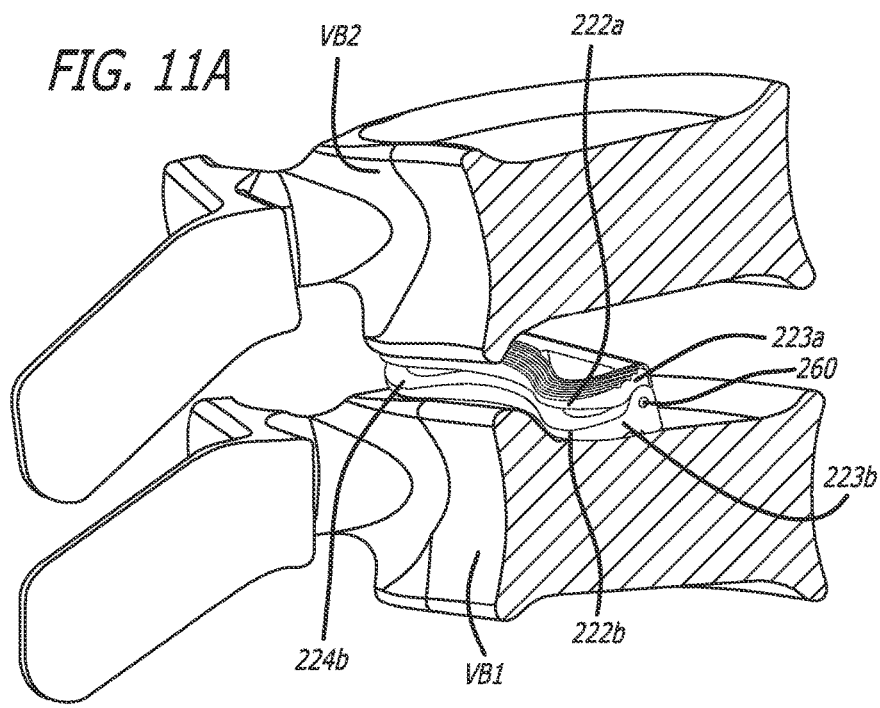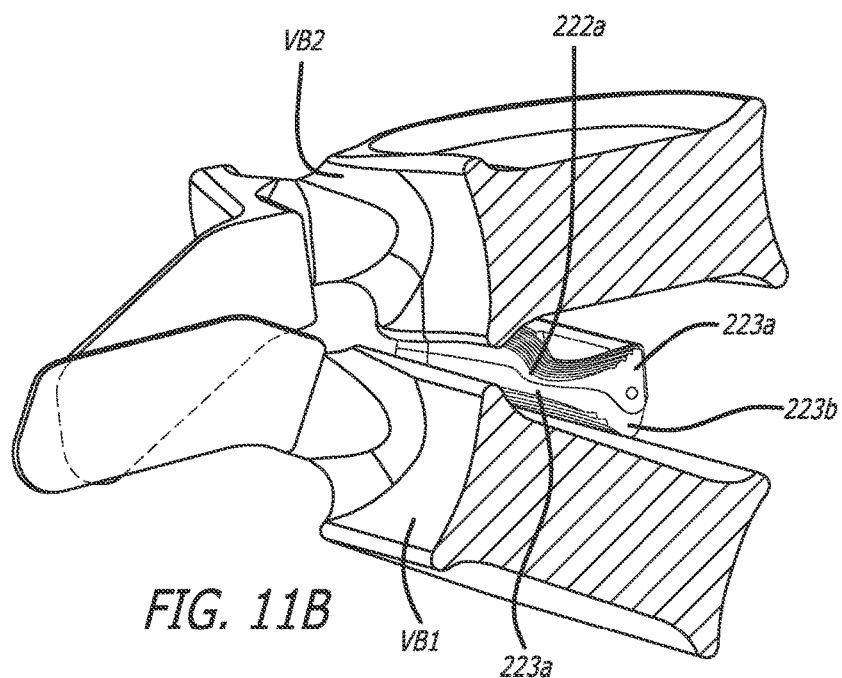

B-SHAPED INTERBODY IMPLANT

BACKGROUND OF THE INVENTION

Field of the Invention

The present invention relates to an interbody implant, specifically to a generally B-shaped spinal implant configured for insertion in a patient's vertebral disc space between two adjacent vertebral bodies, each of the upper and lower adjacent vertebral bodies including an anterior portion and a posterior portion, and more specifically to a generally B-shaped implant configured for placement on bony prominences adjacent the posterior rim of the lower vertebral body.

Description of the Prior Art

Spinal implants, configured for insertion into a patient's disc space between adjacent vertebral bodies are known. A posterior approach to the disc space, and an anterior approach to the disc space are relatively invasive surgeries, involving discomfort, and a relatively long recovery time for the patient.

A lateral or posterior lateral insertion into the disc space, followed by movement of an implant toward the posterior of the disc space, is relatively less invasive, and therefore, in many cases, more desirable. This approach, however, is complicated by the configuration of the adjacent vertebral bodies themselves. For example, the posterior portion of each vertebral body defines a posterior rim. The posterior rim includes numerous adjacent projecting bony prominences, for example, at least two pedicles, two laminae, and several processes, including transverse processes and a posterior spinous process. These bones also define a vertebral foramen, through which the spinal cord passes. A lateral or posterior lateral approach to a position proximate the disc space, followed by movement of the spinal implant posteriorly in the disc space, using traditional spinal implants and traditional lateral approach techniques, often results in interference between the implant and at least one of these bony prominences adjacent the posterior rim of at least one of the adjacent vertebral bodies or soft tissue of the body along the insertion path into the body.

SUMMARY OF THE INVENTION

It is an object of the present invention to provide a spinal implant configured for surgical insertion into a patient's disc space between two adjacent vertebral bodies, and a method of insertion thereof, which substantially obviates one or more of the shortcomings experienced with the prior art.

It is another object of one embodiment of the present invention to provide a generally B-shaped spinal implant having a first end and a second end. The generally B-shaped implant includes a first projecting lobe and a second projecting lobe, the first and second projecting lobes being spaced apart by a concave recess defined therebetween. The concave recess includes an outer surface and an inner surface, the first and second projecting lobes being configured to sit on at least one prominent bone portion of a posterior rim of a lower one of the adjacent vertebral bodies. The concave recess is configured to avoid contact with a vertebral foramen adjacent the posterior rim of the lower one of the adjacent vertebral bodies.

An anterior wall has a first anterior wall portion extending between the first end of the generally B-shaped implant and a position on the inner surface of the concave recess, and a second anterior wall portion extending between the position on the inner surface of the concave recess and the second end of the generally B-shaped implant. The first and second anterior wall portions and the respective first and second projecting lobes define first and second fill spaces therebetween. The first fill space has a first capacity. The first capacity is adapted to receive therein at least a first volume of bone growth material. The second fill space has a second capacity. The second capacity is adapted to receive therein at least a second volume of bone growth matter. At least one of the first and second fill spaces is open to allow bone growth therethrough.

It is a further object of another embodiment of the present invention to provide a spinal implant, wherein the first and second projecting lobes are configured to bear a majority of the load from the upper vertebral body of the adjacent vertebral bodies.

It is a further object of yet another embodiment of the present invention to provide a generally B-shaped spinal implant, configured to have an open configuration anterior of the B-shaped posterior portion of the implant without the enclosed fill spaces described in association with other preferred embodiments of the B-shaped implant. The anteriorly open B-shape allows packing of bone growth material into the first and second fill spaces in the anterior side of the B-shaped posterior portion. These fill spaces can continue into the disc space unimpeded by the anterior wall described in association with other embodiments of the B-shaped implants, if desired.

It is a further object of another embodiment of the present invention to provide an expandable embodiment of the above-described spinal implant, the implant being expandable between an unexpanded position and an expanded position. In this embodiment, the implant is configured for insertion into the disc space in the unexpanded position, and expansion, within the disc space, to the expanded position.

It is a further object of yet another embodiment of the present invention to provide a generally B-shaped spinal implant having at least one truncated end, the at least one truncated end being configured to allow bone graft material into the disc space.

These and other objects of the present invention will be apparent from review of the following specification and the accompanying drawings.

BRIEF DESCRIPTION OF THE DRAWINGS

FIG. 9A is an upper perspective view of another embodiment of a B-shaped spinal implant including a truncated end;

FIG. 9B is an upper side perspective view of the embodiment of the B-shaped spinal implant of FIG. 9A, sitting on a posterior rim of a vertebral body, depicting a flow path of bone graft material past the truncated end of the implant into the disc space;

FIG. 9C is an upper front perspective view of the embodiment of the B-shaped spinal implant of FIG. 9B, sitting on a posterior rim of a vertebral body, depicting a flow path of bone graft material past the truncated end of the implant into the disc space;

FIG. 11A is a side view, partially in cross-section, of the B-shaped implant depicted in FIG. 10B, inserted between two vertebral bodies, the two vertebral bodies defining the first angle of lordosis;

FIG. 11B is an upper perspective view, partially in cross-section, of the B-shaped implant depicted in FIG. 10C, inserted between two vertebral bodies, the two vertebral bodies defining the second angle of lordosis;

DETAILED DESCRIPTION OF THE PREFERRED EMBODIMENTS

Figure 1A:
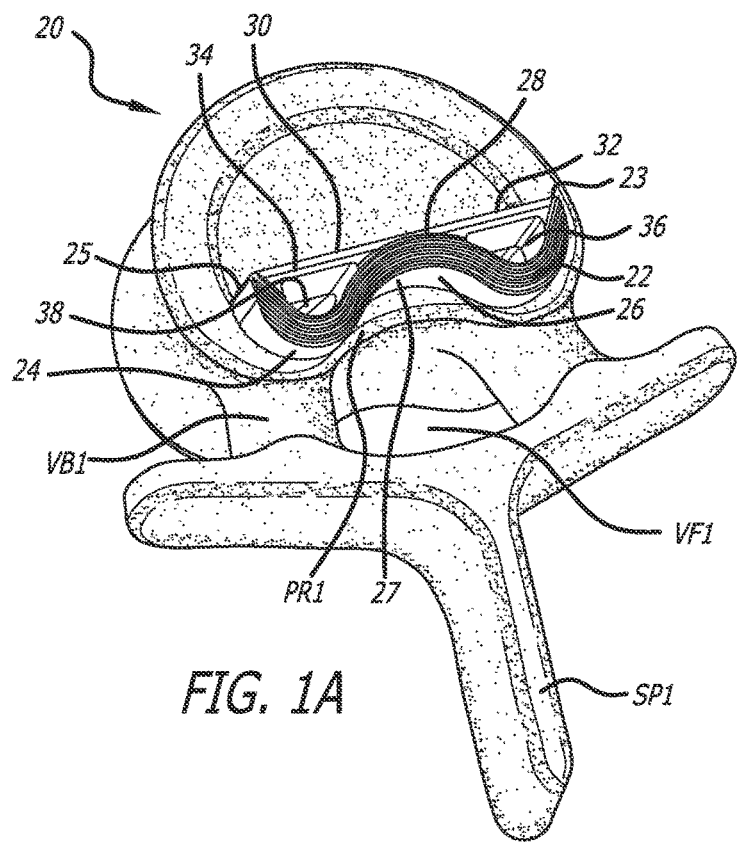
FIG. 1A is an upper perspective view of a preferred embodiment of a B-shaped spinal implant in accordance with the present invention, sitting on a posterior rim of a vertebral body.

In accordance with one embodiment of the invention, and as broadly depicted in FIGS. 1A-3, a B-shaped spinal implant 20 is provided. In this embodiment, spinal implant 20 includes a first projecting lobe 22, a second projecting lobe 24, and a concave recess 26 spacing apart the two lobes 22 and 24. The concave recess 26 includes an outer surface 27, and an inner surface 28. The first and second projecting lobes 22 and 24 are configured to mimic the configuration of, and sit on, bony prominences of a posterior rim PR1 of the lower one VB1 of the two adjacent vertebral bodies. The concave recess 26 is configured to avoid contact with the vertebral foramen VF1 of vertebral body VB1. The B-shaped implant 20 further includes a first end 23 and a second end 25.

Figure 2:
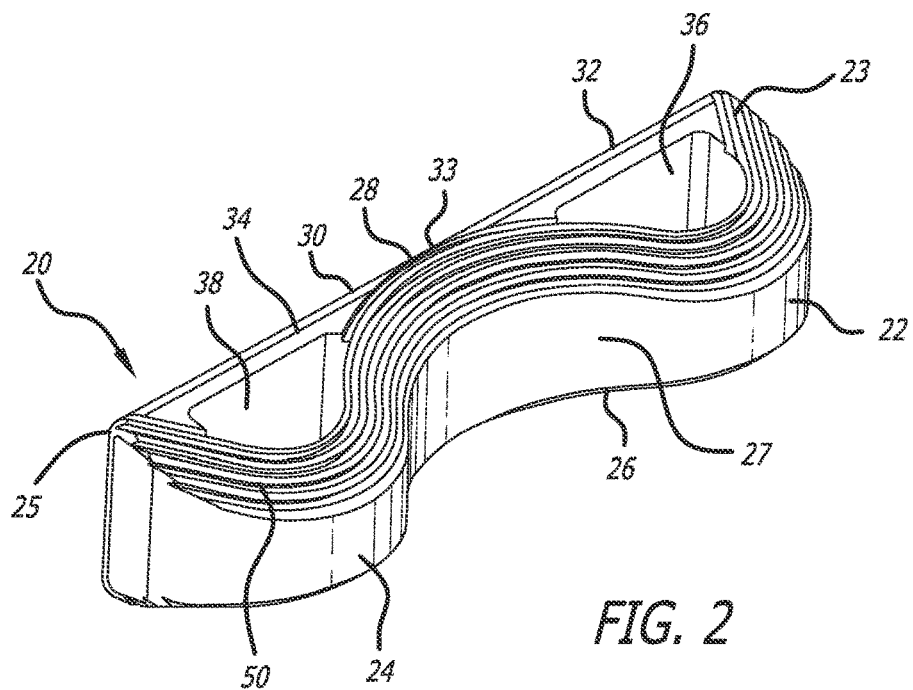
FIG. 2 is an upper perspective view of the preferred embodiment of the B-shaped spinal implant of FIG. 1A.

In the embodiment of FIGS. 1A and 2, an anterior wall 30 extends between the first end 23 and the second end 25. Anterior wall 30 in this embodiment includes two anterior wall portions. First anterior wall portion 32 extends between first end 23 and a position 33 on the inner surface 28 of the concave recess 26. Second anterior wall portion 34 extends between position 33 and the second end 25. In this embodiment, each of the anterior wall portions 32 and 34 are planar. The first anterior wall portion 32 cooperates with the first projecting lobe 22 to define a first fill space 36. First fill space 36 has a first capacity C1 configured to be filled with a first volume V1 of a bone growth material. Suitable bone growth materials, including, but not limited to, autologous bone graft material, allograft bone graft material, and synthetic bone graft materials such as hydroxyapatite, are well known in the art. The second anterior wall portion 34 cooperates with the second projecting lobe 24 to define a second fill space 38. Second fill space 38 has a second capacity C2 configured to be filled with a second volume V2 of the bone growth material. In the embodiment of FIG. 1A, C1=C2 and V1=V2, but the invention does not require equal bone growth material capacities or volumes for the fill spaces 36 and 38.

The first and second projecting lobes 22 and 24 of the B-shaped implant 20 are configured to receive a significant portion of the load applied by vertebral bodies above the disc space. The anterior portion A1 of the disc space between the adjacent vertebral bodies VB1, VB2 can be filled with another implant with or without fusion if desired, or filled with bone or other bone growth promoting material to promote fusion between the adjacent vertebral bodies. In a preferred embodiment, the fill spaces 36 and 38 are open to allow bone growth therethrough from vertebral body to vertebral body. Anterior wall 30 is configured to bear a smaller load than the projecting lobes 22 and 24 of the B-shaped implant 20.

Figure 1B:
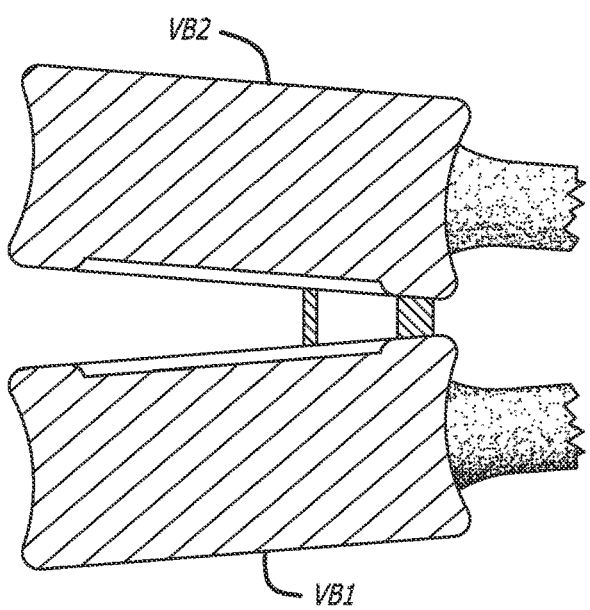
FIG. 1B is a side cross-sectional view of the B-shaped spinal implant in accordance with FIG. 1A, in a disc space between two adjacent vertebral bodies.

As depicted in FIG. 1B, the B-shaped spinal implant 20 is configured to be inserted in a disc space between adjacent vertebral bodies VB1 and VB2. When inserted in the disc space, bone growth material in first fill space 36 allows bone growth between VB1 and VB2.

Figure 3:
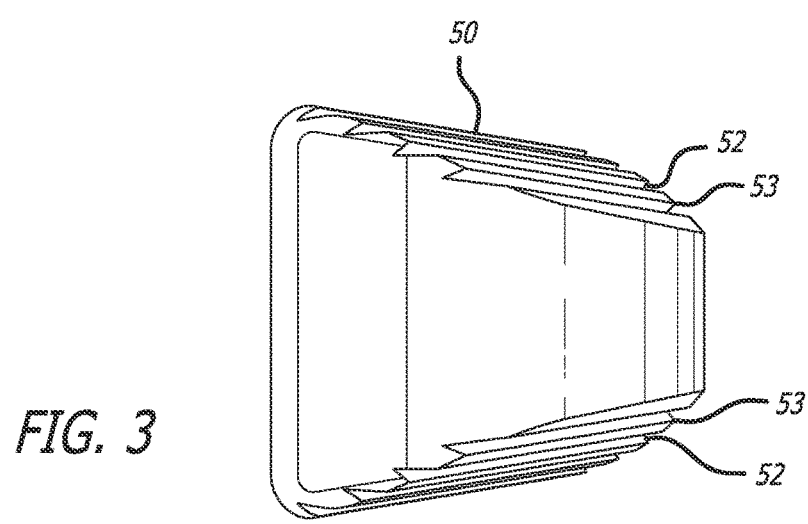
FIG. 3 is a side view of a wedge-shaped configuration of the B-shaped spinal implant of FIG. 1A.

As broadly depicted in FIGS. 2 and 3, the B-shaped implant 20 includes an upper surface 50. Upper surface 50 can be contoured to match the B-shape of implant 20, including the shapes of the first and second projecting lobes 22 and 24, and the concave recess 26. In addition, the upper surface 50 and the lower surface (not shown) can be configured with one or more anti-backout grooves 52, which define teeth 53 configured to engage surfaces on the adjacent vertebral bodies VB1 and VB2, after insertion of the spinal implant 20 into the disc space, to prevent inadvertent backing out of the implant. The ridgeline of the teeth 53 are configured to generally follow the outer perimeter of the spinal implant 20 such that the teeth 53 face the perimeter and thus as the contour of the B-shaped perimeter changes direction so do the teeth 53. This is different from previous spinal implants that typically have the teeth facing the same direction as one another. As depicted in FIG. 3, the B-shaped posterior portion 20, viewed from the side, is wedge-shaped.

Figure 4:
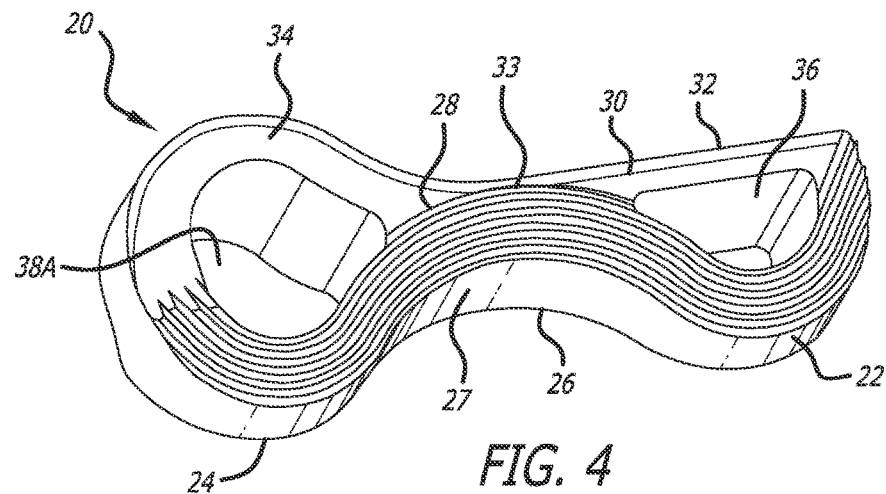
FIG. 4 is an upper perspective view of another embodiment of a B-shaped spinal implant in accordance with the present invention.

In an another preferred embodiment of the invention, as depicted in FIG. 4, the B-shaped implant 20 is configured to have an increased capacity in the second fill space 38A. In this embodiment, the first anterior wall portion 32 is planar, but the second anterior wall portion 34 is arcuate. Arcuate anterior wall portion 34 cooperates with the second projecting lobe 24 to define a second fill space 38A having a third capacity C3, capable of holding a third volume V3 of bone growth material. In this embodiment of the invention, C3 and V3 are greater than C1 and V1, and also greater than C2 and V2.

Figure 5:
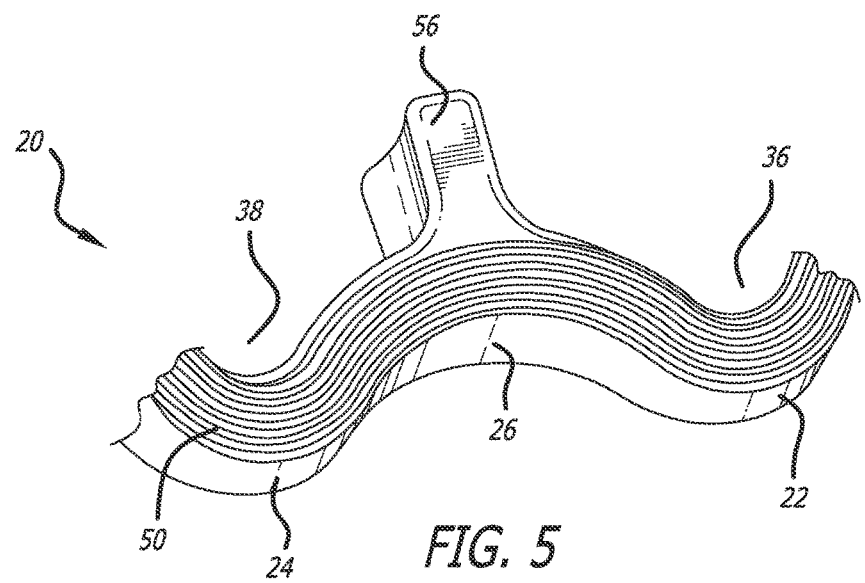
FIG. 5 is an upper perspective view of another embodiment of a B-shaped spinal implant.
Figure 6:
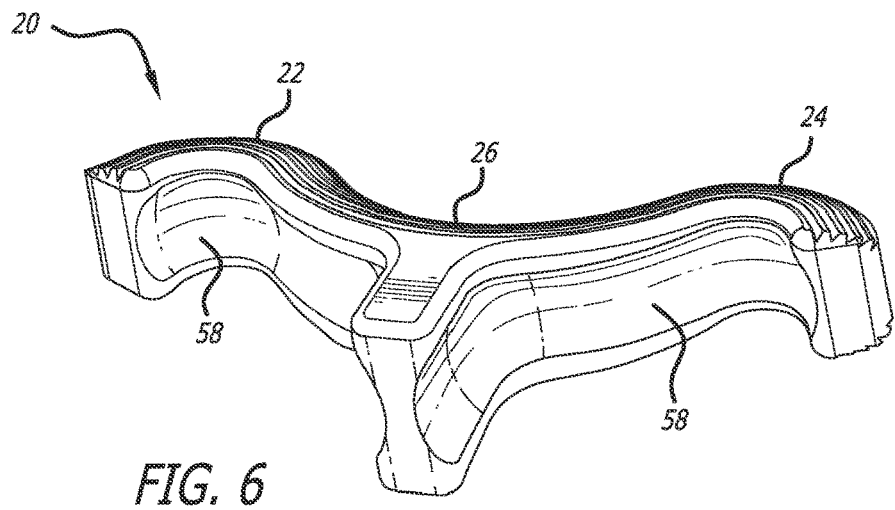
FIG. 6 is an upper perspective view of another embodiment of a B-shaped spinal implant in accordance with the invention.

In another preferred embodiment of the invention, as depicted in FIGS. 5-6, the B-shaped implant 20 is configured to have an open configuration anterior of the B-shaped posterior portion of the implant without the enclosed fill spaces described in association with other preferred embodiments of the B-shaped implant. In the open configuration, the anterior wall 30 is removed or otherwise not included during manufacture, and the first and second projecting lobe portions 22 and 24 are configured to be spread apart. The open configuration still allows pre-packing the first and second fill spaces 36 and 38 with bone growth material before insertion of the B-shaped implant 20 into the disc space. As depicted in FIG. 5, a stabilization leg 56 can be provided in this embodiment, projecting inward from the inner surface 28 of the concave recess 28. In addition, in this embodiment of the invention, as depicted in FIG. 6, the first projecting lobe 22, the second projecting lobe 24, and the stabilization leg 56 have inner surfaces 58, which can be undercut to increase the capacities C1, C2, and C3 of the first fill space 36 and the second fill space 38, respectively.

The above-described embodiments of the invention can be inserted into the patient's body, using a lateral approach, to a position proximate the disc space, and then inserted, in the anterior direction, into the disc space. Unlike in previous implants, the B-shaped implant of the present invention, including the first and second projecting lobes 22 and 24, respectively, are configured to sit on bony prominences at the posterior rim PR1 of the lower vertebral body VB1, and to avoid contact with the vertebral foramen VF1, thereby allowing movement of the implant, posteriorly into the disc space, following a lateral approach, with fewer complications for the surgeon, and less discomfort for the patient.

Figure 7:
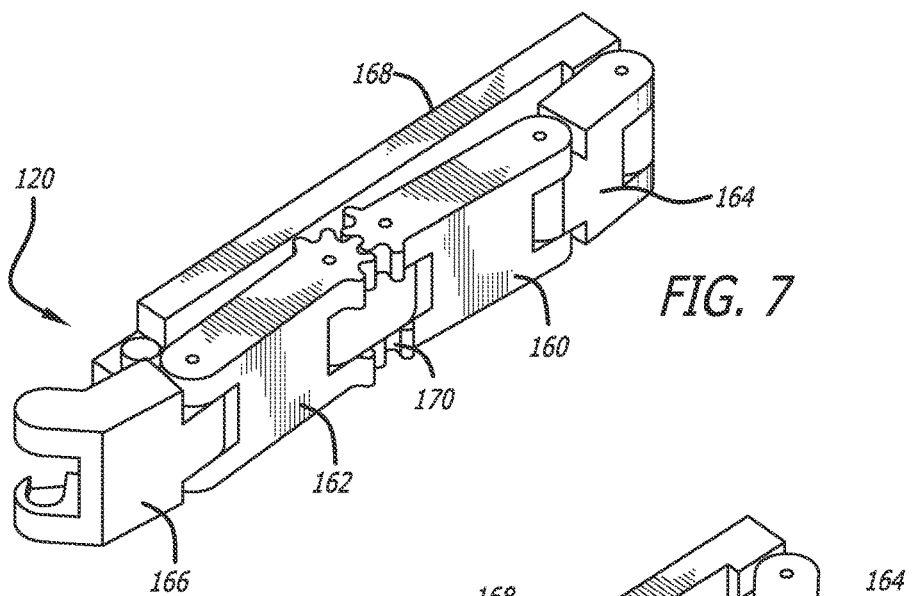
FIG. 7 is an upper perspective view of a preferred embodiment of an expandable B-shaped spinal implant in accordance with the invention, in an unexpanded position.
Figure 8:
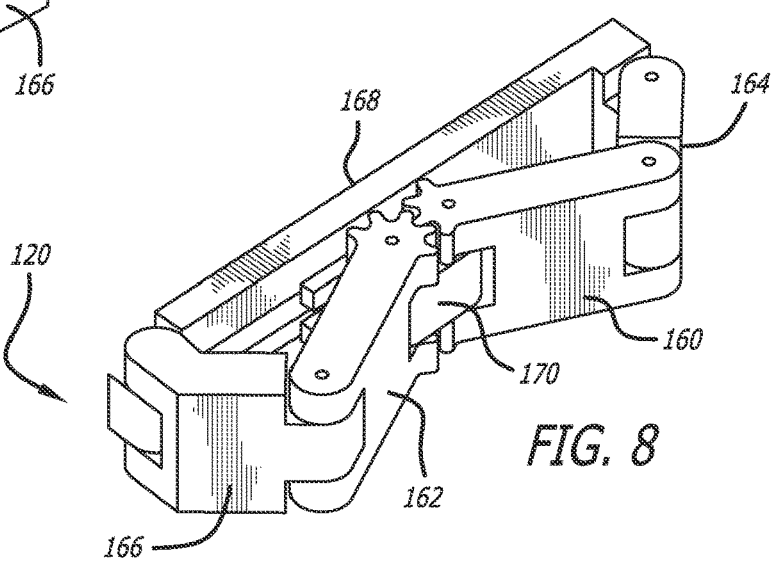
FIG. 8 is an upper perspective view of the preferred embodiment of an expandable B-shaped spinal implant depicted in FIG. 7, in a partially expanded position.

In another embodiment of the present invention, as depicted in FIGS. 7 and 8, the B-shaped spinal implant of the present invention is configured as an expandable implant 120, configured to expand between an unexpanded position, depicted in FIG. 7, and an expanded position, which corresponds generally to the configuration depicted in FIG. 2. A partially-expanded position is depicted in FIG. 8.

In this embodiment of the invention, as depicted in FIGS. 7-8, a first link 160 is pivotally connected to a second link 162. The first link 160 also is pivotally connected to a third link 164. The second link 162 also is pivotally connected to a fourth link 166. A fifth elongated link 168 is provided behind links 160, 162, 164, and 166, and is pivotally connected to each of the third link 164 and the fourth link 166. First link 160 and second link 162 are pivotally attached to one another via a rack and pinion mechanism 170.

Referring to FIG. 8, in this embodiment of the invention, first link 160 and second link 162 pivots inward with respect to one another due to motion of the rack and pinion mechanism 170. Movement of the first link 160 and the second link 162 in turn pivots the third link 164 and the fourth link 166, respectively. Movement of the third link 164 and the fourth link 166 in turn pivots or moves the fifth link 168. Motion of the links as described above expands the expandable implant 120 to the fully-expanded B-shaped implant similar to that as depicted in FIG. 2, with links 160 and 164 defining the first projecting lobe 22, links 162 and 166 defining the second projecting lobe 24, and link 168 defining the anterior wall 30.

Figure 13A:
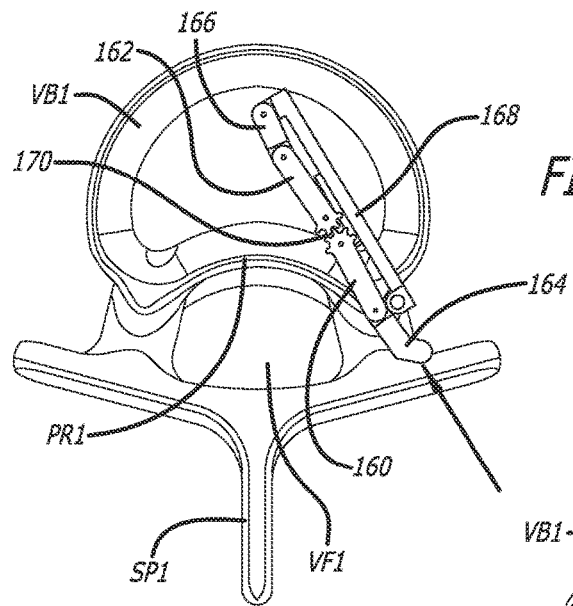
FIGS. 13A-13C are top views depicting a posterior lateral insertion into the disc space of the expandable B-shaped implant in the unexpanded position depicted in FIG. 7, and expansion of the B-shaped implant to the expanded position depicted in FIG. 8 by rotation of the implant in the disc space.
Figure 13B:
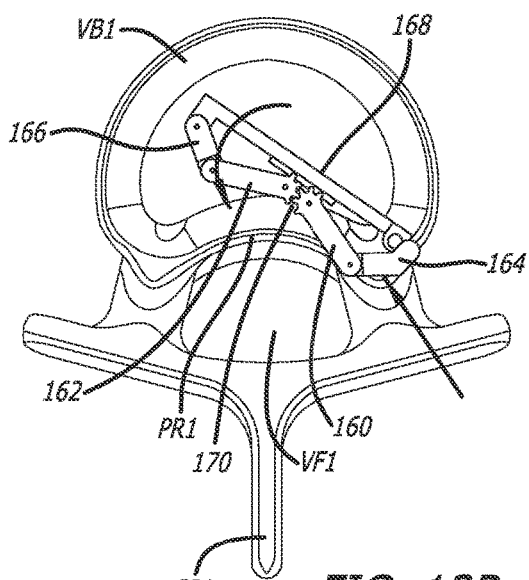
Figure 13C:
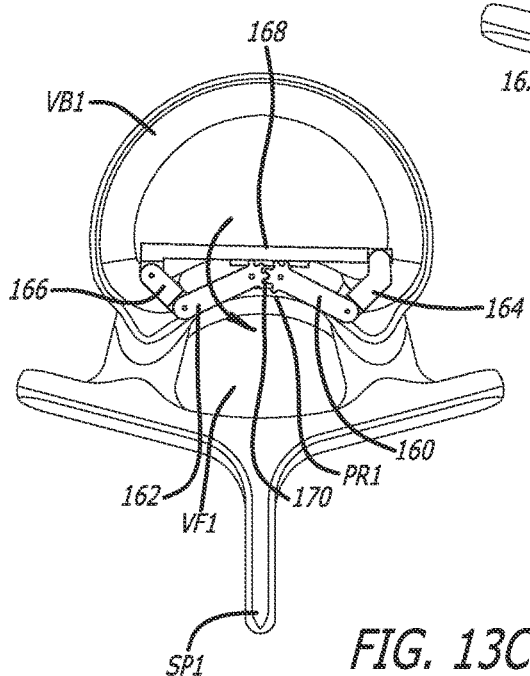

The relatively thin profile of the expandable spinal implant 120, in its unexpanded position assists in easy insertion, of this embodiment into the disc space, using a posterior lateral approach into the disc space, as depicted in FIG. 13A. Once inserted, the expandable spinal implant 120 can be expanded in the disc space, as depicted in FIGS. 13B-13C to the expanded position. In this embodiment of the invention, the expandable implant 120 is configured to be expanded to the expanded position by rotating it while it is in the disc space.

Another embodiment of a B-shaped spinal implant 172 is depicted in FIGS. 9A-9C. In this embodiment of the invention, a B-shaped spinal implant 172 includes a first projecting lobe 174, a second projecting lobe 176, a concave recess 177 separating the two projecting lobes, an anterior wall 178, a first end 180, a second end 182, a first fill space 184, and a second fill space 186. In this embodiment of the invention, as depicted in FIG. 9A, the second end 182, the anterior wall 178, and the second projecting lobe 176 have been truncated to define a truncated end portion 182a. In the embodiment of the invention depicted in FIGS. 9B and 9C, when the B-shaped implant 172 sits on a vertebral body, e.g., vertebral body VB1, the truncated end 182a is configured to allow bone graft material BG1 to bypass the implant 172, and to enter into the disc space along a path represented by an arrow in FIGS. 9B and 9C.

Figure 10A:
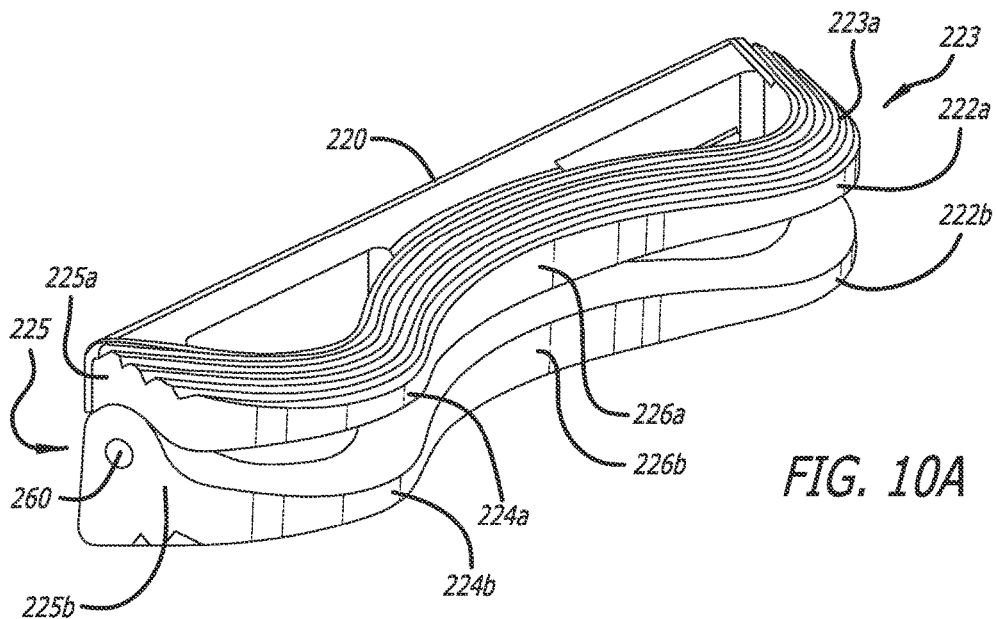
FIG. 10A is an upper perspective view of another embodiment of a B-shaped spinal implant in accordance with the present invention.

Another embodiment of a B-shaped spinal implant 220 is depicted in FIGS. 10A-12B and includes a hinge feature. As depicted in FIG. 10A, hinged B-shaped spinal implant 220 includes a first upper projecting lobe 222a, a first lower projecting lobe 222b a second upper projecting lobe 224a, and a second lower projecting lobe 224b. An upper concave recessed portion 226a connects the first and second upper projecting lobes 222a and 224a. A lower concave recessed portion 226b connects the first and second lower projecting lobes 222b and 224b. The hinged B-shaped spinal implant further includes a first curved end plate 223, divided into upper and lower first end plates 223a and 223b, and a second curved end plate 225, divided into upper and lower second end plates 225a and 225b. The first and second curved endplates 223 and 225 are connected together via a pivot pin 260, which enables the upper projecting lobes 222a and 224a to pivot relative to the lower projecting lobes 222b and 224b. A lock or other mechanism well known in the art for maintaining expandable implants in an expanded position can be used to hold the implant at the desired angle.

Figure 10B:
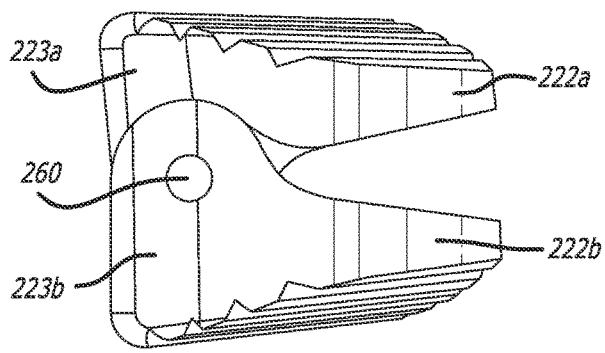
FIG. 10B is a side view of the B-shaped spinal implant of FIG. 10 OA, pivoted to a first position to correspond to at least a first angle of spinal lordosis.

FIGS. 10B and 11A depict B-shaped spinal implant 220, pivoted on an axis defined by pivot pin 260 to a first position, corresponding to a first angle of spinal lordosis.

Figure 10C:
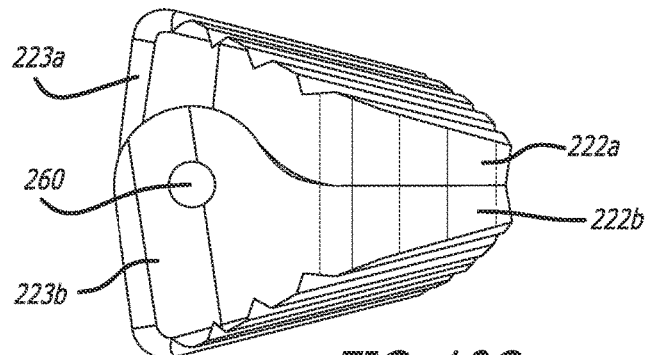
FIG. 10C is a side view of the B-shaped spinal implant of FIG. 10A, pivoted to a second position to correspond to at least a second angle of spinal lordosis.

FIGS. 10C and 11B depict B-shaped spinal implant 220 pivoted on pivot pin 260 to a second position, collapsed posteriorly, corresponding to an increased second angle of lordosis.

Figure 12A:
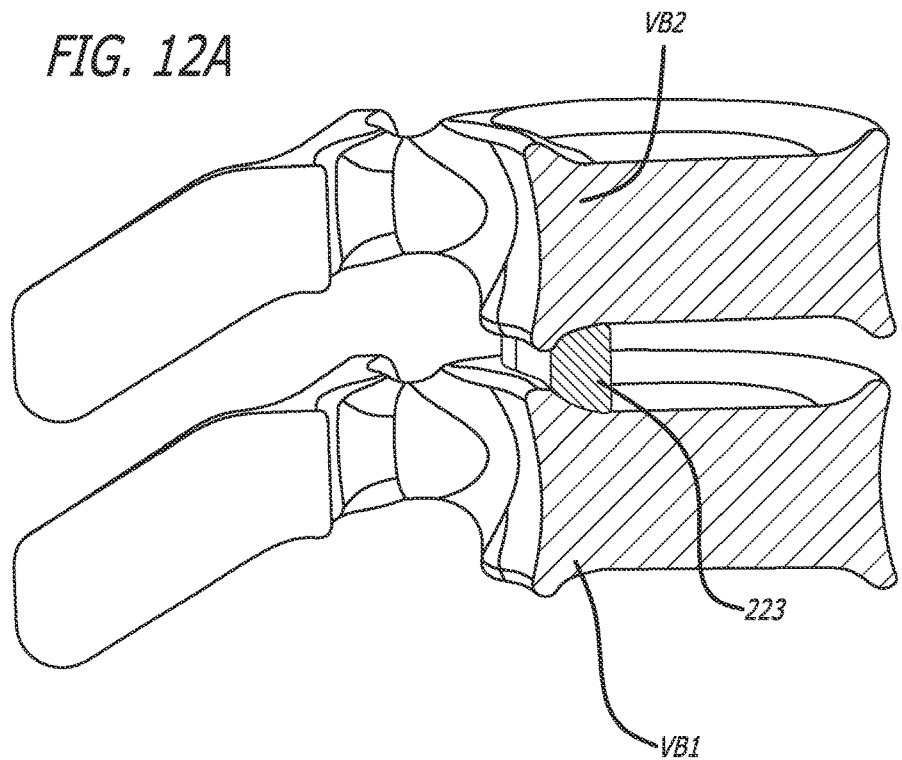
FIG. 12A is an upper perspective view, partially in cross-section, of an endplate of the B-shaped implant depicted in FIG. 10B, inserted between two vertebral bodies, the two vertebral bodies defining a third angle of lordosis.
Figure 12B:
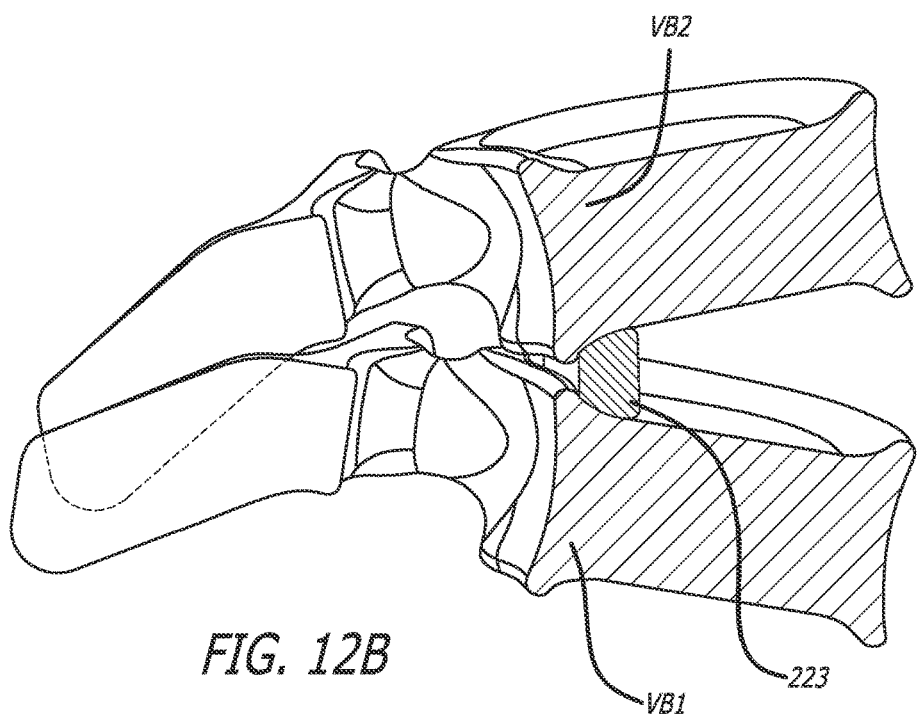
FIG. 12B is a side view, partially in cross-section, of the B-shaped implant depicted in FIG. 10B, inserted between two vertebral bodies, the two vertebral bodies defining a fourth angle of lordosis.

FIGS. 12A and 12B depict B-shaped spinal implant 220 inserted between adjacent vertebral bodies VB1 and VB2, with curved end plate 223 allowing conformance of the implant at least to third and fourth angles of lordosis.

Persons of ordinary skill in the art will recognize that additional modifications can be made to the above-described embodiments of the B-shaped implant, without departing from the spirit or scope of the invention. Features described in association with one preferred spinal implant may be applied to all embodiments of implants described herein, as desired. As an example only, and not as a limitation, in order to increase capacity and volume of the fill spaces 36, 38, 184,186, the undercut portions on the inner surfaces of the projecting lobes can be provided in any of the above-described embodiments. As another example, and not as a limitation, the truncated implant 172 can be truncated on the other end 180, and still be within the scope of the invention. By way of yet additional examples, the truncated feature can be used on the horizontally expandable implant of FIGS. 7 and 8 or with the vertically expandable implant with hinge of FIGS. 10A-12B.

In addition, it is within the scope of the invention to provide bone growth material in preformed packages (not shown). Such preformed packages are configured to fit at least the into the first fill space, and into the second fill space.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An unexpandable spinal implant for surgical insertion in a patient's vertebral disc space between two adjacent vertebral bodies, each of the adjacent vertebral bodies including an anterior portion and a posterior portion, the spinal implant comprising:
    a generally B-shaped portion having a first lateral end and a second lateral end, the generally B-shaped portion including a first projecting lobe and a second projecting lobe, the first projecting lobe having a first convex outer surface, the second projecting lobe having a second convex outer surface, the first and second projecting lobes being spaced apart by a concave portion defined therebetween, the concave portion including a concave outer surface, the first convex outer surface, the second convex outer surface, and the concave outer surface forming a continuous undulating contour, the first and second projecting lobes being configured to sit on at least one prominent bone portion of a posterior rim of a lower one of the adjacent vertebral bodies, the concave portion being configured to substantially avoid contact with a vertebral foramen adjacent the posterior rim of the lower one of the adjacent vertebral bodies; and
    an anterior wall having a first anterior wall portion, a second anterior wall portion, and a substantially planar surface extending along portions of the first and second anterior wall portions, the first and second anterior wall portions and the respective first and second projecting lobes defining respective first and second fill spaces therebetween, the first and second fill portions including respective first and second inner surfaces, the first fill space having a first capacity, the first capacity being adapted to receive therein at least a first volume of a bone growth material, the second fill space having a second capacity, the second capacity being adapted to receive therein at least a second volume of the bone growth material, each of the first and second fill spaces having an upper portion, and a lower portion, at least one of the upper portions and the lower portions being open to allow bone growth therethrough;
    wherein the generally B-shaped portion and the anterior wall are unitarily formed with one another as a rigid construct to receive load from the two adjacent vertebral bodies applied thereto; and
    wherein a first plane extends along the substantially planar surface, a second plane is parallel to the first plane and contacts the first inner surface and the second inner surface at portions thereof farthest from the first plane, a third plane is parallel to the first plane and contacts the concave outer surface at a portion thereof closest to the first plane, and the third plane is closer than the second plane to the first plane.

2. A spinal implant as recited in claim 1, wherein at least the generally B-shaped portion has an upper surface, the upper surface including at least one anti-backout groove defined therein.

3. A spinal implant as recited in claim 2, wherein the at least one anti-backout groove includes a contour, the contour being substantially identical to a contour of the generally B-shaped portion.

4. A spinal implant as recited in claim 1, wherein the generally B-shaped portion has a lower surface, the lower surface including at least one anti-backout groove defined therein.

5. A spinal implant as recited in claim 1, wherein the generally B-shaped portion is substantially wedge-shaped.

6. A spinal implant as recited in claim 1, wherein the first capacity of the first fill space is substantially equal to the second capacity of the second fill space.

7. A spinal implant as recited in claim 1, wherein the first and second projecting lobes are configured to support a first amount of load.

8. A spinal implant as recited in claim 7, wherein the anterior wall is configured to support a second amount of load, the second amount of load being less than the first amount of load.

9. A spinal implant as recited in claim 1, further comprising at least one cartridge of preformed bone growth material, the cartridge being configured to be packed into at least one of the first fill space and the second fill space.

10. An unexpandable spinal implant for surgical insertion in a patient's vertebral disc space between two adjacent vertebral bodies, each of the adjacent vertebral bodies including an anterior portion and a posterior portion, the spinal implant comprising:
    a generally B-shaped portion having a first lateral end, a second lateral end, a first projecting lobe, and a second projecting lobe, the first projecting lobe having a first convex outer surface, the second projecting lobe having a second convex outer surface, the first and second projecting lobes being spaced apart by a concave portion defined therebetween, the concave portion including a concave outer surface, the first convex outer surface, the second convex outer surface, and the concave outer surface forming a continuous undulating contour, the first and second projecting lobes being configured to sit on at least one prominent bone portion of a posterior rim of one of the adjacent vertebral bodies, the concave portion being configured to substantially avoid contact with a vertebral foramen adjacent the posterior rim of the one of the adjacent vertebral bodies, the generally B-shaped portion being configured to carry a first amount of load;
    an anterior wall having a first anterior wall portion, a second anterior wall portion, and a substantially planar surface extending along portions of the first and second anterior wall portions, the first and second anterior wall portions and the respective first and second projecting lobes defining respective first and second fill spaces therebetween, the first and second fill portions including respective first and second inner surfaces, the first and second fill spaces being configured to allow bone growth therethrough, the first fill space having a first capacity, the first capacity being adapted to receive therein at least a first volume of a bone growth material, the second fill space having a second capacity, the second capacity being adapted to receive therein at least a second volume of the bone growth material, the anterior wall being configured to carry a second amount of load;

wherein the generally B-shaped portion and the anterior wall are unitarily formed with one another as a rigid construct; and wherein a first plane extends along the substantially planar surface, a second plane is parallel to the first plane and contacts the first inner surface and the second inner surface at portions thereof farthest from the first plane, a third plane is parallel to the first plane and contacts the concave outer surface at a portion thereof closest to the first plane, and the third plane is closer than the second plane to the first plane.

11. A spinal implant as recited in claim 10, wherein one of the first anterior wall portion and the second anterior wall portion includes an arcuate portion.

12. A spinal implant as recited in claim 10, wherein at least the generally B-shaped portion has an upper surface, the upper surface including at least one anti-backout groove defined therein.

13. A spinal implant as recited in claim 12, wherein the at least one anti-backout groove includes a contour, the contour being substantially identical to a contour of the generally B-shaped portion.

14. A spinal implant as recited in claim 10, wherein the generally B-shaped portion has a lower surface, the lower surface including at least one anti-backout groove defined therein.

15. A spinal implant as recited in claim 10, wherein the generally B-shaped portion is substantially wedge-shaped.

16. A spinal implant as recited in claim 10, wherein the first capacity of the first fill space is substantially equal to the second capacity of the second fill space.

17. A spinal implant as recited in claim 10, further comprising at least one cartridge of preformed bone growth material, the cartridge being configured to be packed into at least one of the first fill space and the second fill space.

\* \* \* \* \*

UNITED STATES PATENT AND TRADEMARK OFFICE
CERTIFICATE OF CORRECTION

Page 1 of 1

PATENT NO.         : 10,149,771 B2
APPLICATION NO.    : 14/931047
DATED              : December 11, 2018
INVENTOR(S)        : Jonathan M. Dewey It is certified that error appears in the above-identified patent and that said Letters Patent is hereby corrected as shown below:

In the Specification

In Column 3, Line 20, delete "FIG. 10 OA," and insert -- FIG. 10A, --, therefor.

In Column 5, Line 15, delete "concave recess 28." and insert -- concave recess 26. --, therefor.

Signed and Sealed this
Twenty-third Day of April, 2019

Andrei Iancu
*Director of the United States Patent and Trademark Office*